(12) United States Patent
Bounouar et al.

(10) Patent No.: US 11,768,134 B2
(45) Date of Patent: Sep. 26, 2023

(54) STATION AND METHOD FOR MEASURING AIRBORNE MOLECULAR CONTAMINATION

(71) Applicant: PFEIFFER VACUUM, Annecy (FR)

(72) Inventors: Julien Bounouar, Annecy (FR); Olivier Le Barillec, Annecy (FR)

(73) Assignee: PFEIFFER VACUUM, Annecy (FR)

( * ) Notice: Subject to any disclaimer, the term of this patent is extended or adjusted under 35 U.S.C. 154(b) by 381 days.

(21) Appl. No.: 17/057,953

(22) PCT Filed: May 21, 2019

(86) PCT No.: PCT/EP2019/063027
§ 371 (c)(1),
(2) Date: Nov. 23, 2020

(87) PCT Pub. No.: WO2019/228844
PCT Pub. Date: Dec. 5, 2019

(65) Prior Publication Data
US 2021/0190647 A1    Jun. 24, 2021

(30) Foreign Application Priority Data

May 28, 2018  (FR) ...................................... 1800562

(51) Int. Cl.
*G01N 1/26*    (2006.01)
*G01N 33/00*   (2006.01)

(52) U.S. Cl.
CPC ........... *G01N 1/26* (2013.01); *G01N 33/0011* (2013.01)

(58) Field of Classification Search
CPC ....................................................... G01N 1/26
See application file for complete search history.

(56) References Cited

U.S. PATENT DOCUMENTS

| 3,043,145 A | 7/1962 | Hoffman |
| 4,090,392 A * | 5/1978 | Smith ...................... G01N 1/26 73/863.33 |

(Continued)

FOREIGN PATENT DOCUMENTS

| CN | 108519254 A | 9/2018 |
| FR | 2 795 517 A1 | 12/2000 |

(Continued)

OTHER PUBLICATIONS

Combined Taiwanese Office Action and Search Report dated Aug. 5, 2022 in Patent Application No. 108117788 (with English language translation), 26 pages.

(Continued)

*Primary Examiner* — Nathaniel J Kolb
(74) *Attorney, Agent, or Firm* — Oblon, McClelland, Maier & Neustadt, L.L.P.

(57) ABSTRACT

A station for measuring airborne molecular contamination includes: at least one gas analyser; a conditioning pump; and a sequencing unit including a sequencing program defining an order for the measurements to be performed for at least two sampling lines, the sequencing unit being configured to control the connection of a sampling line to be measured, the measurement of which is programmed to follow that of a sampling line being measured, with the conditioning pump, while controlling the connection of the sampling line being measured with the at least one gas analyser. A method for measuring airborne molecular contamination using such a station is also disclosed.

5 Claims, 2 Drawing Sheets

Fig.1

(56) References Cited

U.S. PATENT DOCUMENTS

2010/0094565 A1\* 4/2010 Prince .................... G08B 21/12
                                                          702/22
2015/0153299 A1   6/2015 Chou et al.

FOREIGN PATENT DOCUMENTS

KR    10-2011-0026918 A    3/2011
WO       WO 01/79809 A1   10/2001

OTHER PUBLICATIONS

International Search Report dated Aug. 28, 2019 in PCT/EP2019/063027 filed on May 21, 2019, 2 pages.

\* cited by examiner

STATION AND METHOD FOR MEASURING AIRBORNE MOLECULAR CONTAMINATION

BACKGROUND OF THE INVENTION

Field of the Invention

The present invention relates to a station for measuring airborne molecular contamination, particularly intended for monitoring concentrations of molecular contamination in the atmosphere of clean rooms, such as the clean rooms in semiconductor manufacturing plants. The present invention also relates to a method for measuring airborne molecular contamination by means of such a station.

Description of the Related Art

In the semiconductor manufacturing industry, the substrates, such as the semiconductor wafers or the photomasks, must be protected against Airborne Molecular Contamination (AMC) in order to prevent this contamination from damaging the chips or electronic circuits of the substrates. To this end, the substrates are contained in atmospheric transportation and storage cases that allow the substrates to be transported from one item of equipment to another or to be stored between two manufacturing steps. Furthermore, the transportation cases and the equipment are arranged inside clean rooms, in which the level of particles is minimized and the temperature, the humidity and the pressure are maintained at precise levels.

In the clean room, the airborne gaseous species can have different sources and be of different types, for example, acids, bases, condensable elements, doping elements, etc., are encountered. These molecules can originate from the air inside the semiconductor manufacturing plant or can be released, particularly by the semiconductor wafers that have undergone prior manufacturing operations.

Gas analysers present in the clean rooms allow the concentration of airborne gaseous species to be assessed in real-time, particularly the concentration of the humidity and of some acids. The measured concentrations are sometimes very low, such as of the order of ppm or of ppb. With these gas analysers measuring their surrounding gaseous atmosphere, a gas analyser therefore needs to be provided in each test zone of the clean room.

A requirement exists for increasing the number of gaseous species measured and for increasing the number of test zones in order to reduce the risks of contaminating the substrates. However, increasing the number of analysers per zone and increasing these test zones means that this solution quickly becomes very expensive.

In order to reduce costs, a measuring unit has been proposed that consolidates different analysers. The unit is provided with a plurality of input ports, each addressing a particular test zone of the clean room. As the clean rooms can be very big, and with the number of test zones also increasing, a significant number of sampling lines then needs to be used, with the lengths of these lines most often extending to several tens of metres. This long route that is taken by the gas to reach the measuring cell of the analyser is time consuming, which implies a delay in the information. Indeed, the entire volume contained in the sampling line needs to be "replaced" at least once with the gas to be measured, with this gas also being able to easily adhere to the walls of the line by adsorption, particularly for gaseous species to be measured that are referred to as polar species.

It then can be difficult to obtain a measurement that actually represents the concentration of gaseous species in the test zone without waiting a very long time for each change of test zone.

One solution involves simultaneous aspiration in all the sampling lines. All the sampling lines are thus conditioned by means of a common exhaust, with a measurement of the gas concentration being performed in one line at a time. The gas is thus constantly aspirated in all the sampling lines, which particularly allows good degassing of the sampling lines.

Since the number of lines to be simultaneously sampled is high, this solution nevertheless leads to a significant reduction in the pumping rate in each line. The response time in the sampling line in which a measurement is performed is then prolonged compared to a solution in which the entire pumping rate is dedicated to sampling the one line to be measured. Furthermore, the sampling lines are not all the same length. Some lines can be very short and others can be very long. The pumping rates therefore can exhibit significant disparities between the lines. Cases can even occur whereby the difference in length between two lines is so great that a proper pumping rate in one line amounts to a practically zero pumping rate in another line.

One solution could involve increasing the pumping capacity of the simultaneous sampling. However, this would result in a relatively high cost.

One of the aims of the present invention is to propose a measuring station that at least partially resolves the aforementioned disadvantages.

BRIEF SUMMARY OF THE INVENTION

To this end, the aim of the invention is a station for measuring airborne molecular contamination comprising at least one gas analyser and a conditioning pump, characterized in that it further comprises a sequencing unit comprising a sequencing program defining an order for the measurements to be performed for at least two sampling lines, the sequencing unit being configured to control the connection of a sampling line to be measured, for example, a single sampling line, the measurement of which is programmed to follow that of a sampling line being measured, with the conditioning pump, while controlling the connection of the sampling line being measured with the at least one gas analyser.

The sampling line thus can be conditioned under optimum and rapid pumping conditions.

Indeed, the measuring time is reduced since the conditioning of the sampling line is performed in hidden time.

Furthermore, maximum pumping can be used for the conditioning irrespective of the number of sampling lines. The number of sampling lines therefore can be increased without this changing the pumping performance for conditioning. The gas that is thus aspirated before the line is measured allows the sampling line to be degassed. The measurements then can be more precise, particularly in the event that a significant change of concentration has occurred between two zones to be consecutively tested and in the event that a sufficient degassing time is required to obtain a measurement that actually represents the concentration in the test zone.

It is thus possible to measure the concentration of different airborne gaseous species at different points in the clean room using the same set of gas analysers, with the measuring station addressing an input port in each test zone of the clean room, which thus limits the costs.

According to a first embodiment, the measuring station comprises:
- a sampling electrovalve that can be controlled by the sequencing unit on each sampling line;
- a first and a second conditioning electrovalve that can be controlled by the sequencing unit, arranged as a branch of the input of the conditioning pump;
- a first and a second measuring electrovalve that can be controlled by the sequencing unit, arranged as a branch of the input of the at least one gas analyser, the first conditioning electrovalve and the first measuring electrovalve being connected to sampling electrovalves of a first series of sampling lines, the second conditioning electrovalve and the second measuring electrovalve being connected to sampling electrovalves of a second series of sampling lines.

Such a measuring station comprises, for example, at least five sampling electrovalves.

The first series of sampling lines can comprise the same number of sampling lines as the second series.

The sequencing program defines, for example, an order for the measurements to be performed, alternating the measurements to be performed in each series of sampling lines. This solution allows the number of valves that is used to be limited, which allows the device to be simplified and the costs to be managed.

According to a second embodiment, the measuring station comprises:
- a first conditioning electrovalve that can be controlled by the sequencing unit, arranged as a branch of the input of the conditioning pump;
- a first measuring electrovalve that can be controlled by the sequencing unit, arranged as a branch of the input of the at least one gas analyser, the first measuring electrovalve and the first conditioning electrovalve being connected to a sampling line;
- at least one second conditioning electrovalve that can be controlled by the sequencing unit, arranged as a branch of the first conditioning electrovalve and the input of the conditioning pump;
- at least one second measuring electrovalve that can be controlled by the sequencing unit, the at least one second measuring electrovalve being arranged as a branch of the first measuring electrovalve and the input of the at least one gas analyser, the at least one second measuring electrovalve and the at least one second conditioning electrovalve being connected to at least one respective sampling line.

This measuring station comprises, for example, less than four second conditioning electrovalves and less than four second measuring electrovalves A further aim of the invention is a method for measuring airborne molecular contamination by means of a measuring station as previously described, characterized in that a sampling line, for example, a single sampling line, is conditioned, the measurement of which line is programmed to follow that of a sampling line being measured, while measuring in the sampling line with at least one gas analyser.

According to one embodiment of the method for measuring by means of a measuring station according to the first embodiment, the measurements to be performed in each of the two series of sampling lines are alternated, a first series of sampling lines being connected to a first conditioning electrovalve and to a first measuring solenoid valve, a second series of sampling lines being connected to a second conditioning electrovalve and to a second measuring solenoid valve.

BRIEF DESCRIPTION OF THE SEVERAL VIEWS OF THE DRAWINGS

Further features and advantages of the invention will become apparent from the following description, which is provided by way of a non-limiting example, with reference to the accompanying drawings, in which.

Throughout these figures, identical elements use the same reference signs.

DETAILED DESCRIPTION OF THE INVENTION

The following embodiments are examples. Even though the description refers to one or more embodiments, this does not necessarily mean that each reference relates to the same embodiment or that the features are applicable only to one embodiment. Simple features of various embodiments also can be combined in order to provide other embodiments.

Figure 1:
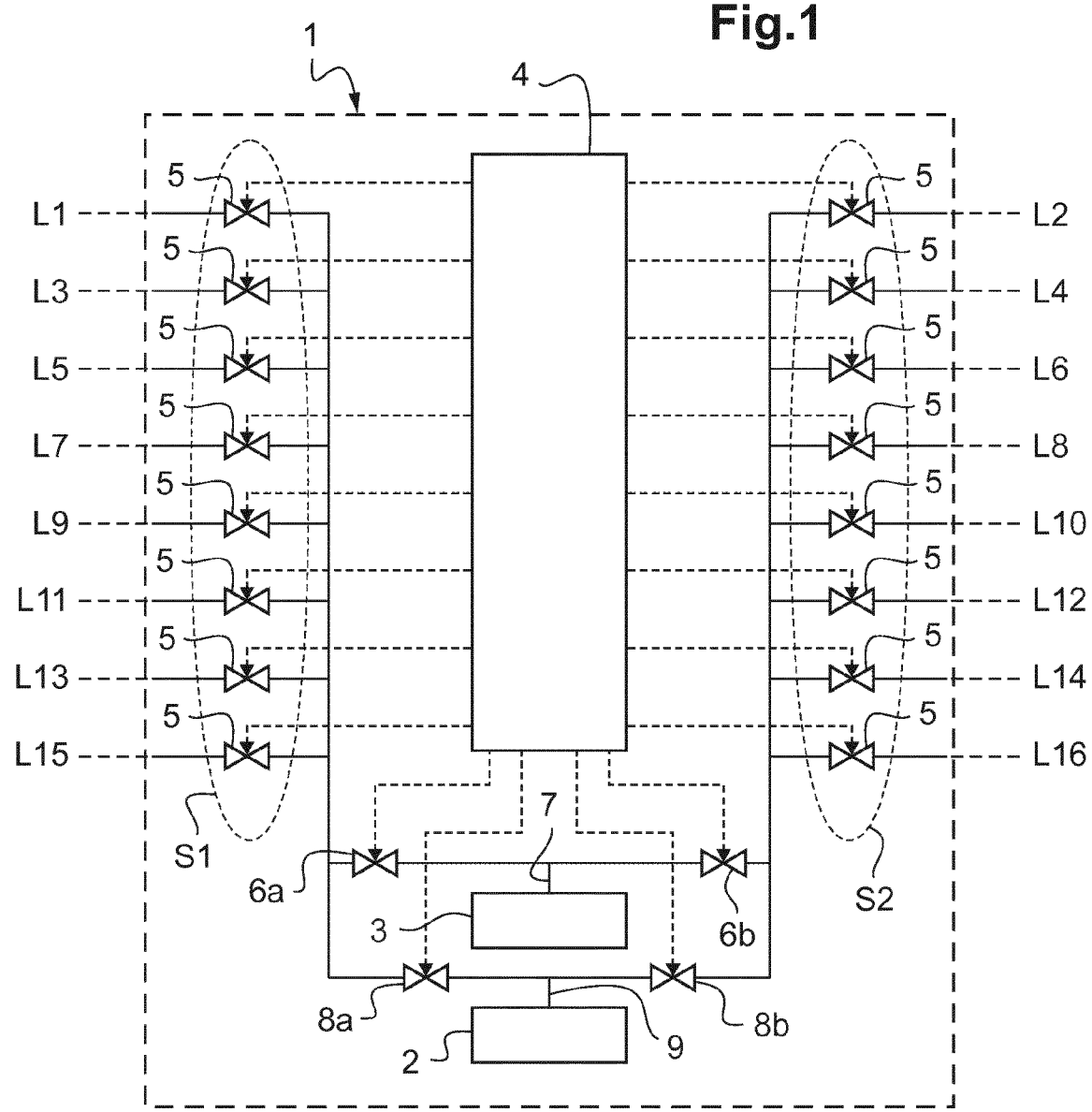
FIG. 1 shows a schematic view of a first embodiment of a station for measuring airborne molecular contamination.

FIG. 1 shows elements of a station 1 for measuring airborne molecular contamination, particularly intended for monitoring concentrations of molecular contamination in the atmosphere of clean rooms, such as the clean rooms in semiconductor manufacturing plants.

The measuring station 1 comprises at least one gas analyser 2, a conditioning pump 3 and a sequencing unit 4.

According to one embodiment, the gas analyser 2 comprises a small sampling pump. The gas analyser 2 allows the concentration of at least one gaseous species to be measured in real-time, i.e. with a measuring time of less than a few seconds, even a few minutes, for low concentrations below ppm or ppb. The measured gaseous species is, for example, an acid, such as hydrofluoric acid HF or hydrochloric acid HCl or a solvent, such as PGMEA (propylene glycol methyl ether). According to another embodiment, the gaseous species is ammonia $NH_3$. A gas analyser 2 can be adapted to measure a distinct gaseous species or a group of distinct gaseous species.

The conditioning pump 3 comprises, for example, a small capacity vacuum pump, such as a small multistage vacuum pump.

The sequencing unit 4 is a computer, for example.

The sequencing unit 4 comprises a sequencing program defining an order for the measurements to be performed for at least two sampling lines from among the sampling lines L1-L16.

The sampling lines L1-L16 comprise, for example, flexible pipes, made of materials limiting the adhesion of the gaseous species to the walls, such as perfluoroalkoxy (also called PFA) or polytetrafluoroethylene (also called PTFE). The sampling lines L1-L16 connect the measuring station 1 to specific test zones of the clean room. The length of the sampling lines L1-L16 can vary between the various test zones to be reached and can be several tens of metres long, for instance between 40 and 200 metres long.

The sequencing program defines the order for the measurements to be performed, i.e. in which order the measurements of concentrations of gaseous species must be performed in the sampling lines L1-L16 connected to the measuring station 1.

The sequencing unit 4 is also configured to control the connection of a sampling line L1-L16, for example, a single sampling line, to be measured with the conditioning pump 3, while it controls the connection of the sampling line L1-L16 being measured with the at least one gas analyser 2.

Thus, a distinction is made between a sampling line "being measured" and a sampling line "to be measured". The sampling line "to be measured" among the sampling lines L1-L16 is the line for which the measurement is programmed to follow that of the sampling line L1-L16 being measured.

To this end, according to a first embodiment shown in FIG. 1, the measuring station 1 comprises:
- a sampling electrovalve 5 that can be controlled by the sequencing unit 4 on each sampling line L1-L16;
- a first and a second conditioning electrovalve 6a, 6b that can be controlled by the sequencing unit 4, arranged as a branch of the input 7 of the conditioning pump 3; and
- a first and a second measuring electrovalve 8a, 8b that can be controlled by the sequencing unit 4, arranged as a branch of the input 9 of the at least one gas analyser 2.

A plurality of gas analysers 2, for measuring concentrations of different gases or groups of gaseous species, can be connected to the input 9 in order to simultaneously sample from the same sampling line.

The first conditioning electrovalve 6a and the first measuring electrovalve 8a are connected to sampling electrovalves 5 of a first series S1 of sampling lines L1, L3, L5, L7, L9, L11, L13, L15. The first series S1 of sampling lines comprises at least one sampling line.

The second conditioning electrovalve 6b and the second measuring electrovalve 8b are connected to sampling electrovalves 5 of a second series S2 of sampling lines L2, L4, L6, L8, L10, L12, L14, L16. The second series S2 of sampling lines comprises at least one sampling line.

For example, there are at least five sampling lines L1-L16, each provided with a sampling electrovalve 5, for instance sixteen sampling lines L1-L16. The first series S1 of sampling lines comprises, for example, the same number of sampling lines as the second series S2 (eight in the example).

The sequencing program defines, for example, an order for the measurements to be performed that alternate the measurements to be performed in each series S1, S2 of sampling lines. This solution allows the number of valves that is used to be limited, which allows the device to be simplified and the costs to be managed.

During operation, a sampling line L1-L16 is conditioned, for example, a single sampling line, the measurement of which is programmed to follow that of a sampling line L1-L16 being measured, while a measurement is performed in the sampling line L1-L16 with the at least one gas analyser 2. For example, the measurements to be performed in each of the two series 51, S2 of sampling lines are alternated.

By taking, for example, a sequencing program 100 that defines that a measurement of the concentration of gaseous species must be performed in sampling line L5 of the first series S1, followed by a measurement in sampling line L4 of the second series S2, the sampling line L4 of the second series S2 is conditioned, while a measurement is performed in the sampling line L5 with the at least one gas analyser 2.

To this end, the sequencing unit 4 controls the connection of sampling line L4 with the conditioning pump 3 by opening the sampling electrovalve 5 of sampling line L4, as well as the second conditioning electrovalve 6b, with the first conditioning electrovalve 6a connected to the sampling electrovalves 5 of the first series S1 being closed.

Figure 2:
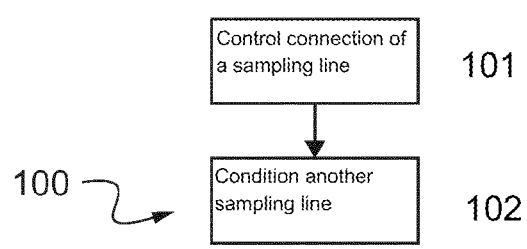
FIG. 2 shows a schematic view of a method for measuring airborne molecular contamination by means of the measuring station of FIG. 1.

At the same time, the sequencing unit 4 controls the connection of sampling line L5 with the at least one gas analyser 2 by opening the sampling electrovalve 5 of sampling line L5, as well as the first measuring electrovalve 8a, with the second measuring electrovalve 8b connected to the sampling electrovalve 5 of the second series S2 being closed (step 101, FIG. 2).

Then, after having performed the measurement in sampling line L5, the sequencing unit 4 controls the connection of sampling line L4 with the at least one gas analyser 2 by opening the sampling electrovalve 5 of the sampling line L4, as well as the second measuring electrovalve 8b, with the first measuring electrovalve 8a connected to the sampling electrovalves 5 of the first series S1 being closed.

At the same time, the sequencing unit 4 controls the connection of the sampling line of the first series S1, for which a consecutive measurement must be performed of the concentration of the gaseous species, with the conditioning pump 3 (step 102, FIG. 2).

The operations can continue thus until all the measurements defined in the sequencing program are performed in the order. These operations can be repeated as a loop.

It is thus possible to measure the concentration of different airborne gaseous species at different points of the clean room using the same set of gas analysers 2, with the measuring station 1 addressing an input port in each test zone of the clean room, which thus limits the costs.

The sampling lines therefore can be conditioned under optimum and rapid pumping conditions.

Indeed, the measuring time is reduced as the conditioning of the sampling line is performed concurrently.

Furthermore, maximum pumping can be used for the conditioning irrespective of the number of sampling lines. The number of sampling lines therefore can be increased without this changing the pumping performance for conditioning. The gas that is thus aspirated before the line is measured allows the sampling line to be degassed. The measurements then can be more precise, particularly in the event that a significant change of concentration has occurred between two zones to be consecutively tested and in the event that a sufficient degassing time is required to obtain a measurement that actually represents the concentration in the test zone.

Figure 3:
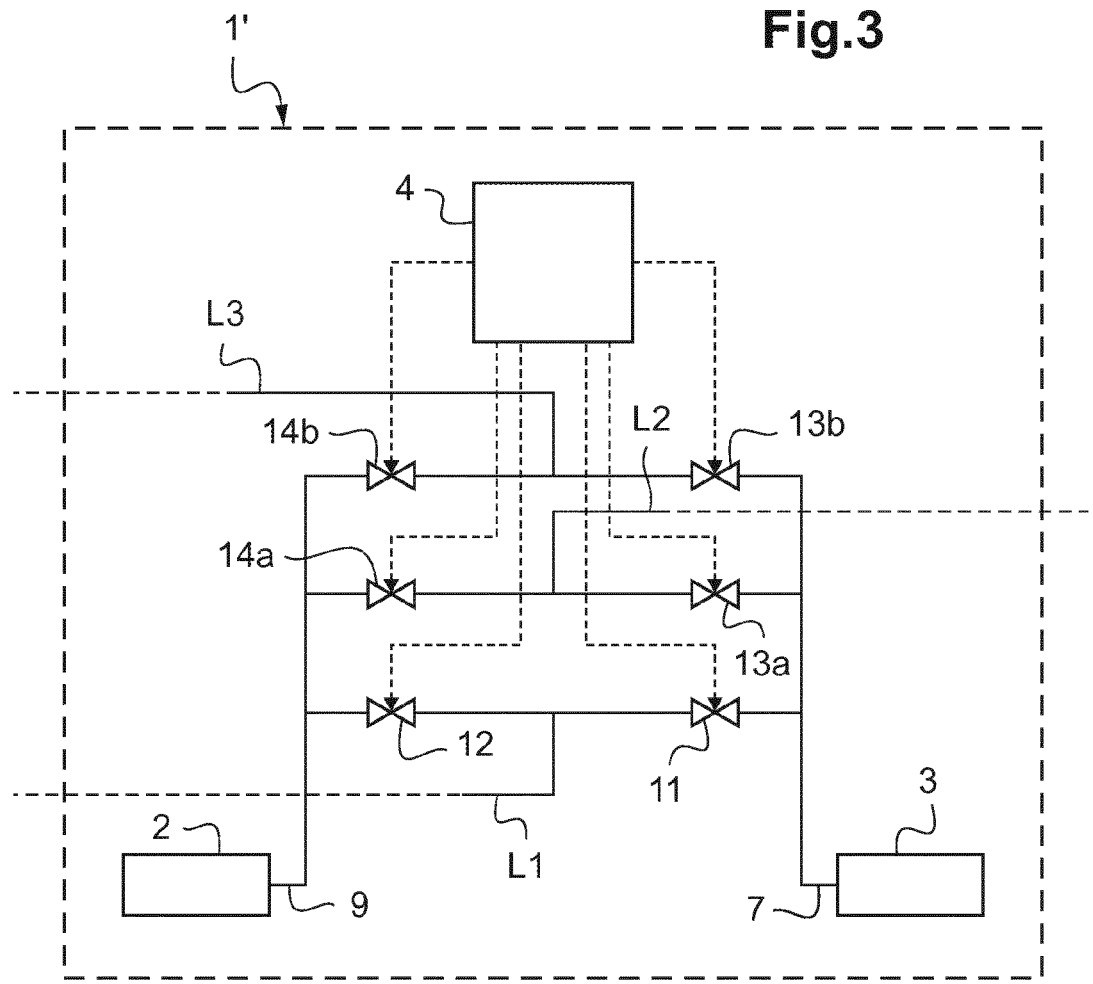
FIG. 3 shows a schematic view of a second embodiment of a station for measuring airborne molecular contamination.

FIG. 3 shows a second embodiment of the measuring station 1'.

In this embodiment, the measuring station 1' comprises:
- a first conditioning electrovalve 11 that can be controlled by the sequencing unit 4, arranged as a branch of the input 7 of the conditioning pump 3;
- a first measuring electrovalve 12 that can be controlled by the sequencing unit 4, arranged as a branch of the input 9 of the at least one gas analyser 2;
- at least one second conditioning electrovalve 13a, 13b that can be controlled by the sequencing unit 4, arranged as a branch of the first conditioning electrovalve 11 and the input 7 of the conditioning pump 3; and
- at least one second measuring electrovalve 14a, 14b that can be controlled by the sequencing unit 4, arranged as a branch of the first measuring electrovalve 12 and the input 9 of the at least one gas analyser 2.

The first measuring electrovalve 12 and the first conditioning electrovalve 11 are connected to a sampling line L1.

The at least one second measuring electrovalve 14a, 14b and the at least one second conditioning electrovalve 13a, 13b are connected to at least one sampling line L2, L3.

The illustrated example has three sampling lines L1-L3, i.e. two second conditioning electrovalves 13a, 13b arranged as a branch of the first conditioning electrovalve 11 and the input 7 of the conditioning pump 3, and two second measuring electrovalves 14a, 14b arranged as a branch of the first measuring electrovalve 12 and the input 9 of the at least one gas analyser 2.

The two second measuring electrovalves 14a, 14b and the two second conditioning electrovalves 13a, 13b are connected to two respective sampling lines L2, L3.

Provision is made, for example, for the measuring station 1' according to this second embodiment to comprise less than four second conditioning electrovalves and less than four second measuring electrovalves, with the measuring station 1 being connected to at most five sampling lines L1-L5. Indeed, beyond five, the number of electrovalves that is required increases the cost of the measuring station 1' fairly significantly.

During operation, a sampling line is conditioned, for example, a single sampling line, the measurement of which is programmed to follow that of a sampling line being measured, while a measurement is performed in the sampling line with the at least one gas analyser 2.

By taking, by way of an example, a sequencing program 100 that defines that a measurement of the concentration of gaseous species must be performed in the sampling line L2, followed by a measurement in the sampling line L3, the sampling line L3 is conditioned, while a measurement is performed in the sampling line L2 with the at least one gas analyser 2.

To this end, the sequencing unit 4 controls the connection of the sampling line L3 with the conditioning pump 3 by opening the second sampling electrovalve 13b of the sampling line L3, with the second measuring electrovalve 14b of the sampling line L3 being closed.

Figure 4:
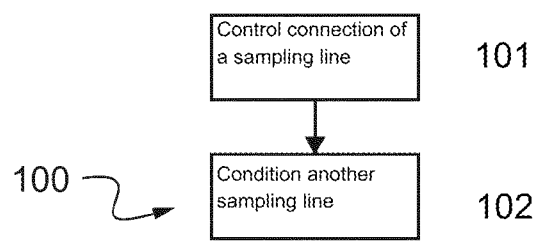
FIG. 4 shows a schematic view of a method for measuring airborne molecular contamination by means of the measuring station of FIG. 3.

At the same time, the sequencing unit 4 controls the connection of the sampling line L2 with the at least one gas analyser 2 by opening the second measuring electrovalve 14a of the sampling line L2, with the second sampling electrovalve 13a being closed (step 101, FIG. 4).

Then, after having performed the measurement in the sampling line L2, the sequencing unit 4 controls the connection of the sampling line L3 with the at least one gas analyser 2 by opening the second measuring electrovalve 14b of the sampling line L3 and by closing the second sampling electrovalve 13b of the sampling line L3 and the second measuring electrovalve 14a of the sampling line L2.

At the same time, the sequencing unit 4 controls the connection of the sampling line, for which a consecutive measurement must be performed of the concentration of gaseous species, with the conditioning pump 3 (step 102, FIG. 4).

The operations can continue thus until all the measurements defined in the sequencing program are performed in the order. These operations can be repeated as a loop.

The invention claimed is:

1. A station for measuring airborne molecular contamination comprising:
   at least one gas analyser;
   a conditioning pump;
   a sequencing unit configured to execute a sequencing program defining an order for measurements to be performed for at least two sampling lines;
   a sampling electrovalve on each sampling line, wherein each sampling electrovalve is controlled by the sequencing unit;
   a first and a second conditioning electrovalve that can be controlled by the sequencing unit, arranged as a branch of an input of the conditioning pump; and
   a first and a second measuring electrovalve that can be controlled by the sequencing unit, arranged as a branch of an input of the at least one gas analyser, the first conditioning electrovalve and the first measuring electrovalve being connected to sampling electrovalves of a first series of sampling lines, the second conditioning electrovalve and the second measuring electrovalve being connected to sampling electrovalves of a second series of sampling lines,
   wherein the sequencing unit being configured to
   control a connection of a sampling line of the first series of sampling lines to be measured by opening the sampling electrovalve of the sampling line of the first series of sampling lines and the first measuring electrovalve, and closing the second measuring electrovalve,
   control a connection of a sampling line of the second series of sampling lines to be measured by opening the sampling electrovalve of the sampling line of the second series of sampling lines and the second measuring electrovalve, and closing the first measuring electrovalve, and
   during measuring of the sampling line of the first or second series of sampling lines with the at least one gas analyser, condition the sampling line of the other of the first or second series of sampling lines with the conditioning pump.

2. The measuring station according to claim 1, wherein the station comprises at least five sampling electrovalves.

3. The measuring station according to claim 1, wherein the first series of sampling lines comprises the same number of sampling lines as the second series.

4. The measuring station according to claim 1, wherein the sequencing program defines an order for the measurements to be performed, alternating the measurements to be performed in each series of sampling lines.

5. A method for measuring airborne molecular contamination using a measuring station according to claim 1, comprising:
   measuring a sampling line of the first series of sampling lines with the at least one gas analyser; and
   while measuring the sampling line with the at least one gas analyser, conditioning a sampling line of the second series of sampling lines.

* * * * *